US010539870B2

(12) United States Patent
Williams, III et al.

(10) Patent No.: US 10,539,870 B2
(45) Date of Patent: Jan. 21, 2020

(54) PHOTORESISTS COMPRISING CARBAMATE COMPONENT

(71) Applicant: Rohm and Haas Electronic Materials, LLC, Marlborough, MA (US)

(72) Inventors: William Williams, III, Ipswich, MA (US); Cong Liu, Shrewsbury, MA (US); Cheng-Bai Xu, Southboro, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 13/907,789

(22) Filed: May 31, 2013

(65) Prior Publication Data

US 2014/0356785 A1 Dec. 4, 2014

(51) Int. Cl.
*G03F 7/004* (2006.01)
*C07C 269/04* (2006.01)
*C07C 271/24* (2006.01)
*G03F 7/039* (2006.01)

(52) U.S. Cl.
CPC .......... *G03F 7/0045* (2013.01); *C07C 269/04* (2013.01); *C07C 271/24* (2013.01); *G03F 7/0397* (2013.01); *G03F 7/0046* (2013.01); *G03F 7/0392* (2013.01)

(58) Field of Classification Search
CPC ........ G03F 7/20; C07C 269/04; C07C 271/24
USPC ..... 430/270.1, 913, 942, 919, 332; 514/275, 514/484; 560/115, 157
See application file for complete search history.

(56) References Cited

U.S. PATENT DOCUMENTS

| 6,486,058 B1 | 11/2002 | Chun |
| 6,607,870 B2 | 8/2003 | Thackeray et al. |
| 7,379,548 B2 | 5/2008 | Revital et al. |
| 8,507,175 B2 * | 8/2013 | Hatakeyama et al. ..... 430/270.1 |
| 2011/0027718 A1 * | 2/2011 | Sato et al. ................. 430/286.1 |
| 2011/0039209 A1 | 2/2011 | Masuyama et al. |
| 2011/0065040 A1 * | 3/2011 | Masuyama et al. ....... 430/270.1 |
| 2011/0065047 A1 * | 3/2011 | Masuyama et al. ....... 430/281.1 |
| 2011/0091812 A1 * | 4/2011 | Hatakeyama et al. ..... 430/284.1 |
| 2011/0223535 A1 | 9/2011 | Liu et al. |
| 2012/0058428 A1 | 3/2012 | Hatakeyama et al. |
| 2012/0077120 A1 | 3/2012 | Prokopowicz et al. |
| 2012/0141938 A1 * | 6/2012 | Hatakeyama et al. ..... 430/283.1 |
| 2012/0183904 A1 * | 7/2012 | Sagehashi et al. ........ 430/285.1 |
| 2013/0165422 A1 * | 6/2013 | Bartsch et al. .......... 514/210.18 |

FOREIGN PATENT DOCUMENTS

| JP | 2011-057663 A | 3/2011 |
| JP | 2011-197067 A | 10/2011 |
| JP | 2012-072062 A | 4/2012 |
| JP | 2012-073279 A | 4/2012 |
| JP | 2012-073606 A | 4/2012 |
| JP | 2012-137729 A | 7/2012 |

OTHER PUBLICATIONS

Machine translation of JP 2011-197067 (no date).*
English Language Summary of Office Action issued in Counterpart Taiwan Appliccation No. 104-2(6)01242-10420360370, dated Mar. 23, 3015 (2 Pages).
English Language Summary of Office Action issued in counterpart Japanese Application No. 2014-110877, dated Dec. 15, 2017 (3 Pages).

* cited by examiner

*Primary Examiner* — Amanda C. Walke
(74) *Attorney, Agent, or Firm* — Mintz Levin Cohn Ferris Glovsky and Popeo, P.C.; Peter F. Corless

(57) ABSTRACT

New photoresist compositions are provided that comprise a carbamate compound that comprises 1) a carbamate group and 2) an ester group. Preferred photoresists of the invention may comprise a resin with acid-labile groups; an acid generator compound; and a carbamate compound that can function to decrease undesired photogenerated-acid diffusion out of unexposed regions of a photoresist coating layer.

24 Claims, No Drawings

PHOTORESISTS COMPRISING CARBAMATE COMPONENT

BACKGROUND

This invention relates to photoresist compositions that comprise a carbamate compound that comprises 1) a carbamate group and 2) an ester group. Preferred photoresists of the invention may comprise a resin with acid-labile groups; an acid generator; and a carbamate compound that can function to decrease undesired photogenerated-acid diffusion out of unexposed regions of a photoresist coating layer.

Photoresists are photosensitive films for transfer of images to a substrate. They form negative or positive images. After coating a photoresist on a substrate, the coating is exposed through a patterned photomask to a source of activating energy, such as ultraviolet light, to form a latent image in the photoresist coating. The photomask has areas opaque and transparent to activating radiation that define an image desired to be transferred to the underlying substrate.

Known photoresists can provide features having resolution and size sufficient for many existing commercial applications. However for many other applications, the need exists for new photoresists that can provide highly resolved images of sub-quarter-micron (<0.25 µm) dimension.

Various attempts have been made to alter the make-up of photoresist compositions to improve performance of functional properties. Among other things, a variety of basic compounds have been reported for use in photoresist compositions. See, e.g., U.S. Pat. Nos. 6,486,058, 6,607,870 and 7,379,548, as well as Japanese published patents JP 1103086 and 1231538. See also U.S. 2011/0223535, US 2012/0077120 and US 2012/0141938.

Short-wavelength imaging such as 193 nm also has been utilized to produce highly resolved small features. Extreme ultraviolet (EUV) and e-beam imaging technologies also have been employed. See U.S. Pat. No. 7,459,260. EUV utilizes short wavelength radiation, typically between 1 nm to 40 nm, with 13.5 nm radiation often employed.

EUV photoresist development continues to be a challenging issue for EUV Lithography (EUVL) technology implementation. Required are development of materials that can provided highly resolved fine features, including low linewidth roughness (LWR), and sufficient sensitivity to afford wafer throughput.

SUMMARY

The present invention provides photoresist compositions comprising a resin, an acid generator, and a carbamate-containing compound that comprises 1) a carbamate group and 2) an ester group.

Preferred carbamate compounds can function as a photoacid diffusion control agent during lithographic processing of a photoresist composition coating layer. Such diffusion control may be suitable assessed by improved resolution of a developed relief image of a resist that comprises the amide compound relative to the relief image of an otherwise comparable resist that does not contain the amide compound.

Preferred carbamate compounds may comprise carbamate groups and/or ester groups that are acid labile.

In certain preferred aspects, a carbamate compound corresponds to the following Formula I:

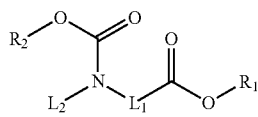

wherein:
R1 and R2 are each the same or different non-hydrogen substituent;
L1 is a linker group that comprises at least one carbon atom;
L2 is hydrogen or a non-hydrogen substituent; and
wherein:
L2 and R2 may be optionally taken together to form a ring structure;
L1 and L2 may be optionally taken together to form a ring structure;
R1 and L1 or R1 and L2 may be optionally taken together to form a ring structure; and
at least one of R1 and R2 comprises an acid-labile moiety.

In that Formula I, preferably each of R1 and R2 comprises a separate acid-labile moiety. For instance, R1 and and/or R2 may comprise an acetal or ester acid-labile group. For ester acid-labile groups, R1 and R2 may suitably comprise a tertiary alkyl group.

References herein that R1 and/or R2 may comprise an acid-labile moiety include both where 1) R1 and/or R2 contain an acid-labile group that does not include any other atom depicted in Formula I above (or below in any of Formulae IA, IB and IC) e.g. where R1 and/or R2 contains a t-butyl ester and 2) where R1 and/or R2 contain a moiety that combines with a —OC(=O)— moiety as depicted above in Formula I (or below in any of Formulae IA, IB and IC) to thereby form an acid-labile moiety such as where R1 and/or R2 is t-butyl or methyladamantyl that thereby links a quaternary carbon to the —OC(=O)— moiety as depicted above in Formula I (or below in any of Formula IA, IB and IC) to form an acid-labile group.

In certain preferred aspects, where R1 and/or R2 comprise an acid-labile group, R1 and/or R2 are a moiety such a t-butyl that forms an acid-labile group with the —OC(=O)— moiety as depicted above in Formula I or below in any of Formulae IA, IB and IC.

In certain aspects, in Formula (I), L1 and L2 may form a non-aromatic (alicyclic) ring. For instance, L1 and L2 may be taken together to form a 5-membered or 6-membered ring that includes the depicted nitrogen as a ring member.

In certain aspects, R2 and L2 may form a non-aromatic (alicyclic) ring. For instance, R2 and L2 may be taken together to form a 5 or 6 membered ring that includes the depicted oxygen as a ring member.

In certain aspects, as mentioned, substituents may be taken together to form a ring structure. In certain preferred aspects, L1 and L2 may be taken together to form a ring (e.g. alicyclic 5 or 6 membered ring which includes the depicted nitrogen as a ring member) and further optionally R1 may link to that ring to form a bicyclic fused ring structure.

Thus, in certain aspects, preferred are carbamate compounds of the following Formula IA:

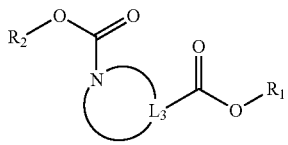

IA wherein in Formula IA, R1 and R2 are the same as disclosed herein for Formula I:

the depicted two semi-circular lines between N and L3 together represent an optionally substituted single-ring or multiple-ring structure having 5 to 20 atoms with N and one or more atoms of L3 being ring members; and L3 contains 1 to 16, more typically 1 to 8, or 1, 2, 3 or 4, carbon or hetero (N, O or S) atoms. For certain aspects, L3 contains only carbon atoms. For instance, L3 suitably may be $CH$, or $CHCH_2$ or $CHCH_2CH_2$.

In particular aspects, preferred are carbamate compounds where N and L3 are ring members of 5-membered or 6-membered rings, such as compounds of the following Formulae IB and IC:

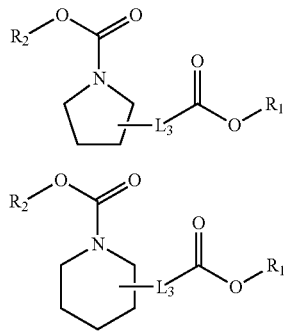

IB

IC wherein in each of Formulae IB and IC, each of R1, R2 and L3 are the same as defined above for Formula IA.

Preferred carbamate compounds of the invention for use in photoresists may be polymeric or non-polymeric, with non-polymeric carbamate compounds preferred for many applications. Preferred carbamate compounds may have relatively low molecular weight, for example, a molecular weight of less than or equal to 3000, more preferably ≤2500, ≤2000, ≤1500, ≤1000, ≤800 or even more preferably ≤500.

Photoresists of the invention may be either positive-acting or negative-acting, and preferably are positive-acting.

In a preferred aspect, photoresists of the invention used for short-wavelength imaging applications, such as 193 nm as well as EUV or e-beam imaging.

Particularly preferred photoresists of the invention may be used in immersion lithography applications.

Methods are also provided for forming relief images of photoresist compositions of the invention (including patterned lines with sub-50 nm or sub-20 nm dimensions). Substrates such as a microelectronic wafer also are provided having coated thereon a photoresist composition of the invention.

We have found that use of a present carbamate compound in a photoresist composition, including chemically-amplified photoresist compositions, can significantly enhance resolution of a relief image (for example, fine lines) of the resist. In particular, we have found that a carbamate compound as disclosed herein imparts significantly enhanced lithographic results, including relative to a comparable photoresist that is otherwise identical to the photoresist that instead contains a different basic additive. Use of a carbamate compound as disclosed herein also can provide improved shelf life to photoresists containing the compound.

DETAILED DESCRIPTION

Carbamate Compounds

As stated above, in certain preferred aspects, a carbamate compound of the present invention corresponds to the following Formula I:

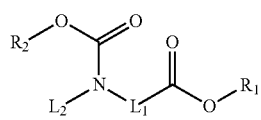

I wherein:
R1 and R2 are each the same or different non-hydrogen substituent;
L1 is a linker group that comprises at least one carbon atom;
L2 is hydrogen or a non-hydrogen substituent;
and wherein:
L2 and R2 may be optionally taken together to form a ring structure;
L1 and L2 may be optionally taken together to form a ring structure;
R1 and L1 or R1 and L2 may be optionally taken together to form a ring structure; and
at least one of R1 and R2 comprises an acid-labile moiety.

References made herein to a "ring structure" (including as the term "ring structure" is recited in any of Formulae I, IA, IB and IC) without further limitation include both single ring groups as well as multiple ring groups that may comprise bi-, tri- or larger structures of fused, spiro, bridged or otherwise linked ring groups.

As referred to herein, acid-labile groups or moieties are those such as ester or acetal that can produce a more polar group (e.g. —OH, or —COO— such as from an ester or —OH) upon lithographic processing, i.e. exposure to activating radiation, such as 193 nm, EUV radiation, e-beam radiation or other radiation sources, typically together with a post-exposure thermal treatment.

In Formulae I, IA, IB and IC above, suitable R1 and R2 moieties include those independently chosen from optionally substituted ($C_1$-$C_{30}$)alkyl, optionally substituted ($C_1$-$C_{30}$)heteroalkyl (such as ($C_1$-$C_{30}$)alkoxy, ($C_1$-$C_{30}$)alkylsulfide, ($C_1$-$C_{30}$)alkylsulfinyl or ($C_1$-$C_{30}$)alkylsulfonyl), optionally substituted carboalicyclic (all ring members of the non-aromatic ring being carbon), optionally substituted heteroalicyclic (one or more ring members of the non-aromatic ring being N, O or S), and optionally substituted carbocyclic aryl such as optionally substituted phenyl, naphthyl or anthracenyl. In certain preferred aspects, R1 and R2 are the same or different optionally substituted ($C_1$-$C_{30}$) alkyl, optionally substituted carboalicyclic or optionally substituted heteroalicyclic.

In Formula I above, L1 suitably contains at least one carbon atom and suitably may contain 1 to about 12 carbon atoms and 1 to about 6 hetero (N, O or S) atoms. L1 groups also may be optionally substituted.

In Formula I above, L2 is suitably hydrogen or a non-hydrogen substituent such as optionally substituted ($C_1$-$C_{30}$) alkyl, optionally substituted ($C_1$-$C_{30}$)heteroalkyl (such as ($C_1$-$C_{30}$)alkoxy, ($C_1$-$C_{30}$)alkylsulfide, ($C_1$-$C_{30}$)alkylsulfinyl or ($C_1$-$C_{30}$)alkylsulfonyl), optionally substituted carboalicyclic (all ring members of the non-aromatic ring being carbon), optionally substituted heteroalicyclic (one or more ring members of the non-aromatic ring being N, O or S), and optionally substituted carbocyclic aryl such as optionally substituted phenyl, naphthyl or anthracenyl.

Also, as discussed above, each of L2 and R2; L1 and L2; and R1 and L1 or R1 and L2, may be optionally taken together along with the atoms to which they are attached to form a ring structure e.g. an optionally substituted 4- to 30-membered heterocyclic single ring or multiple-ring structure.

For R1, R2 and L2, suitable carboalicyclic groups may have 5 to about 30 carbon atoms in a single ring or multi fused or bridged ring structure such as cyclopentyl, cyclohexyl, cycloheptyl, cyclooctyl, and adamantyl. For R1, R2 and L2, suitable heteroalicyclic groups may have 5 to about 30 carbon atoms and 1 to 6 or more hetero (N, O, or S) atoms in a single ring or multi fused or bridged ring structure such as tetrahydofuran. For R1, R2 and L2, preferred carbocyclic groups include phenyl, naphthyl and anthracenyl.

As stated, R1, R2, L1, L2 and L3 may be moieties that are optionally substituted. Substituted moieties are suitably substituted at one or more available positions by e.g. carboxyl (—$CO_2H$); carboxy($C_1$-$C_{30}$)alkyl; ($C_1$-$C_{30}$)alkyl; ($C_1$-$C_{30}$) alkoxy; sulfonyl; sulfonic acid; sulfonate ester; cyano; halo; keto, carbocyclic aryl such as phenyl, napthyl or anthracenyl; heteroaromatic such as $C_{5-30}$ heteroaromtic containing 1-3 N, O or S ring atoms; carboalicyclic (all ring members of the non-aromatic ring being carbon); and optionally substituted heteroalicyclic (one or more ring members of the non-aromatic ring being N, O or S). Preferred substituent groups are carboxyl, carboxy($C_1$-$C_{10}$)alkyl, ($C_1$-$C_{10}$)alkoxy, sulfonyl, sulfonic acid, sulfonate ester, cyano, halo, and keto; and more preferably carboxyl, carboxy($C_1$-$C_8$)alkyl, ($C_1$-$C_8$)alkoxy, sulfonyl, sulfonic acid, sulfonate ester, cyano, halo, and keto. Preferred ester groups (carboxyalkyl) are carboxy($C_1$-$C_6$)alkyl. Preferred alkoxy groups are ($C_1$-$C_6$)alkoxy, and more preferably ($C_1$-$C_5$)alkoxy. By "substituted," it is meant that one or more hydrogens on e.g. a carbon atom of the carbamate compound is replaced with one or more of the above substituent groups. A mixture of such substituent groups may be used. The presence of such substituent groups may impart desired solubility to the amide compound, or may be used to tailor the quenching ability of the carbamate compound.

When any of L2 and R2; L1 and L2; and R1 and L1 or R1 and L2, R1 are taken together along with the atoms to which they are attached to form a heterocyclic ring, they may form a single heterocyclic ring, or multiple rings which may be fused, bridged, or spirocyclic. It is preferred that when L1 and L2 are taken together along with the atoms to which they are attached that an optionally substituted 4- or 5- to 10-membered ring is formed, and more preferably an optionally substituted 5- to 8-membered ring, and even more preferably an optionally substituted 5 to 6-membered ring.

Specifically preferred carbamate compounds for use in photoresist compositions as disclosed herein include the following:

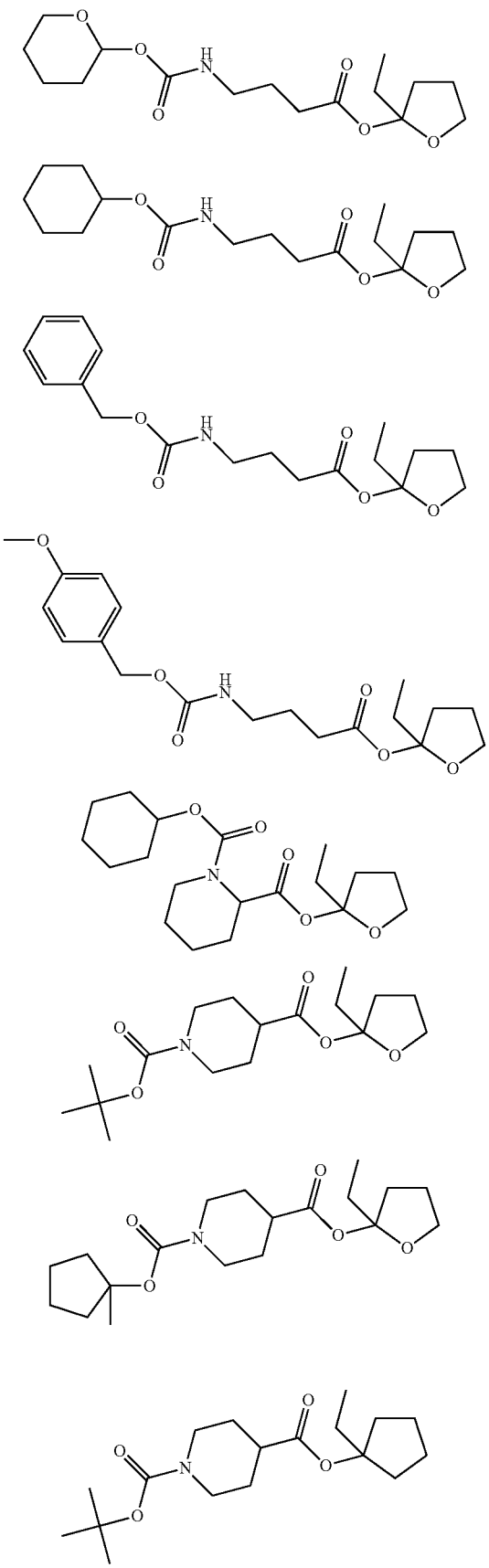

-continued
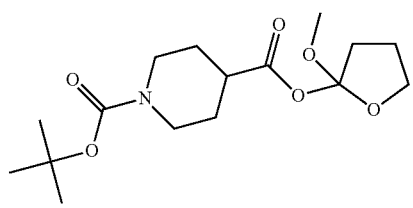
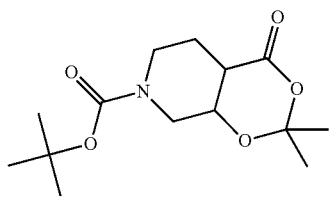
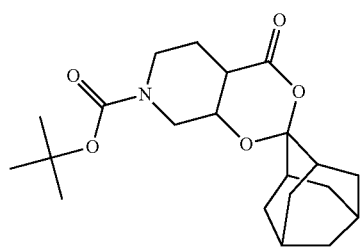
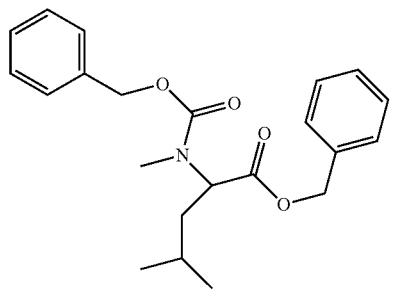
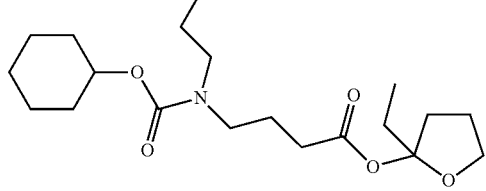
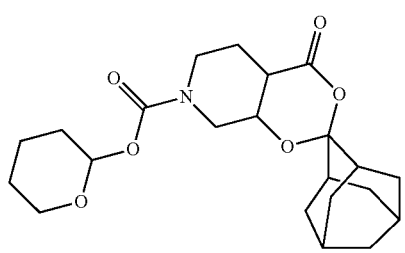
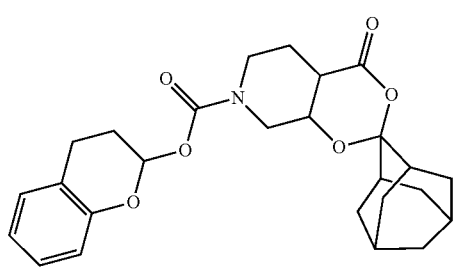
-continued
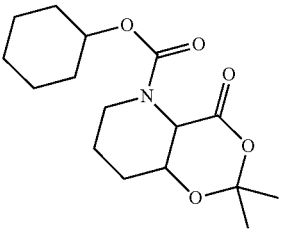
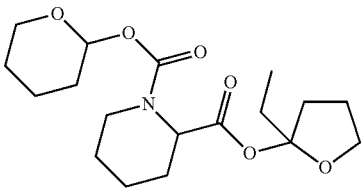
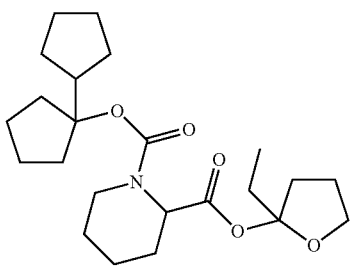
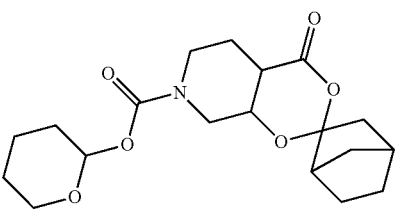
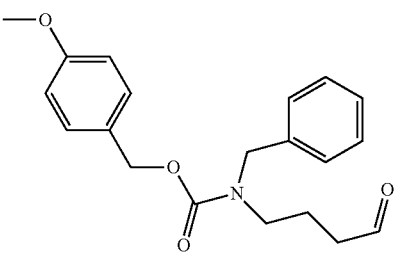
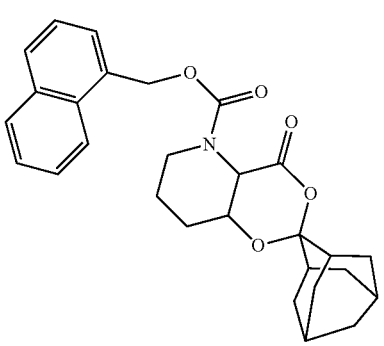

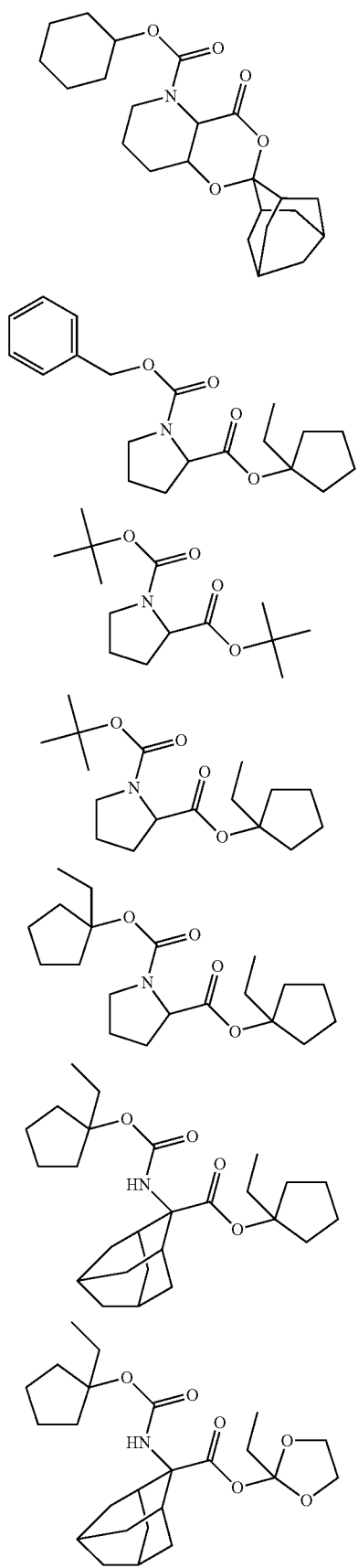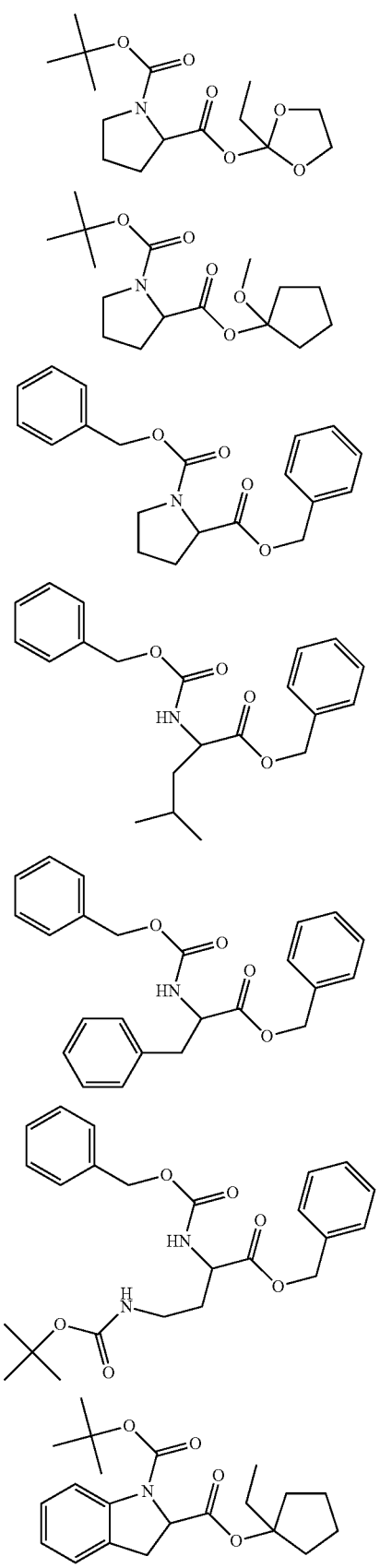

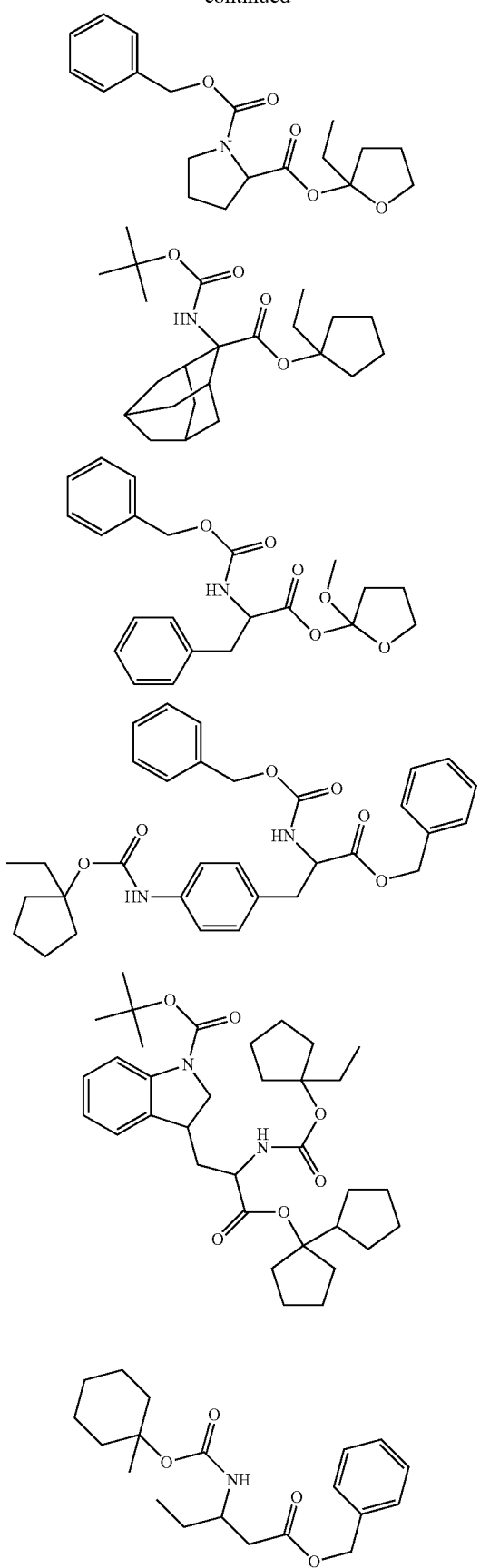
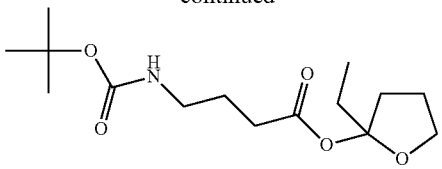
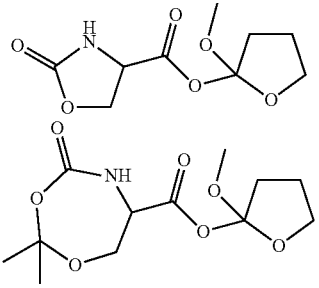
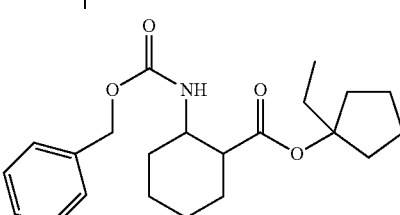
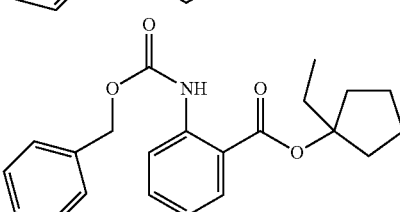
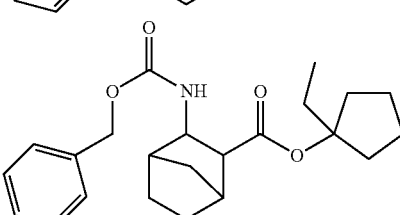
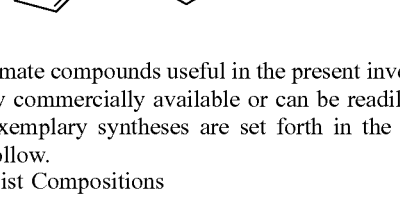
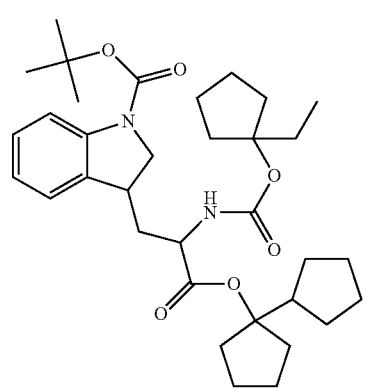
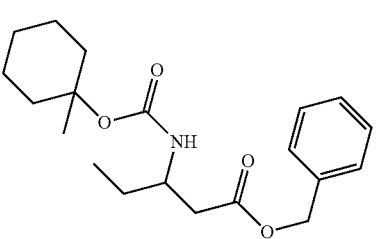

Carbamate compounds useful in the present invention are generally commercially available or can be readily synthesized. Exemplary syntheses are set forth in the examples which follow.

Photoresist Compositions

Photoresists of the invention typically comprise a polymer, one or more acid generators and one or more carbamate compounds as disclosed herein. Preferably the resist polymer has functional groups that impart alkaline aqueous solubility to the resist composition. For example, preferred are polymers that comprise polar functional groups such as hydroxyl or carboxylate, or acid-labile groups that can liberate such polar moieties upon lithographic processing. Preferably the polymer is used in a resist composition in an amount sufficient to render the resist developable with an aqueous alkaline solution.

Acid generators are also suitably used with polymers that comprise repeat units containing aromatic groups, such as optionally substituted phenyl including phenol, optionally substituted naphthyl, and optionally substituted anthracene. Optionally substituted phenyl (including phenol) containing polymers are particularly suitable for many resist systems, including those imaged with EUV and e-beam radiation. For positive-acting resists, the polymer also preferably contains one or more repeat units that comprise acid-labile groups. For example, in the case of polymers containing optionally substituted phenyl or other aromatic groups, a polymer may comprise repeat units that contain one or more acid-labile moieties such as a polymer that is formed by polymerization of monomers of an acrylate or methacrylate compound with acid-labile ester (e.g. t-butyl acrylate or t-butyl methacrylate). Such monomers may be copolymerized with one or more other monomers that comprise aromatic group(s) such as optionally phenyl, e.g. a styrene or vinyl phenol monomer.

Preferred monomers used for the formation of such polymers include: an acid-labile monomer having the following formula (V), a lactone-containing monomer of the following formula (VI), a base-soluble monomer of the following formula (VII) for adjusting dissolution rate in alkaline developer, and an acid-generating monomer of the following formula (VIII), or a combination comprising at least one of the foregoing monomers:

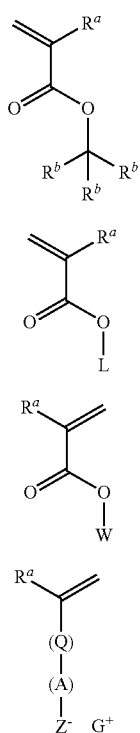

(V)

(VI)

(VII)

(VIII)

wherein each $R^a$ is independently H, F, —CN, $C_{1-10}$ alkyl, or $C_{1-10}$ fluoroalkyl. In the acid-deprotectable monomer of formula (V), $R^b$ is independently $C_{1-20}$ alkyl, $C_{3-20}$ cycloalkyl, $C_{6-20}$ aryl, or $C_{7-20}$ aralkyl, and each $R^b$ is separate or at least one $R^b$ is bonded to an adjacent $R^b$ to form a cyclic structure. In lactone-containing monomer of formula (VI), L is a monocyclic, polycyclic, or fused polycyclic $C_{4-20}$ lactone-containing group. In the base solubilizing monomer of formula (VII), W is a halogenated or non-halogenated, aromatic or non-aromatic $C_{2-50}$ hydroxyl-containing organic group having a pKa of less than or equal to 12. In the acid generating monomer of formula (VIII), Q is ester-containing or non-ester containing and fluorinated or non-fluorinated and is $C_{1-20}$ alkyl, $C_{3-20}$ cycloalkyl, $C_{6-20}$ aryl, or $C_{7-20}$ aralkyl group, A is ester-containing or non-ester-containing and fluorinated or non-fluorinated, and is $C_{1-20}$ alkyl, $C_{3-20}$ cycloalkyl, $C_{6-20}$ aryl, or $C_{7-20}$ aralkyl, $Z^-$ is an anionic moiety comprising carboxylate, sulfonate, an anion of a sulfonamide, or an anion of a sulfonimide, and $G^+$ is a sulfonium or iodonium cation.

Exemplary acid-deprotectable monomers include but are not limited to:

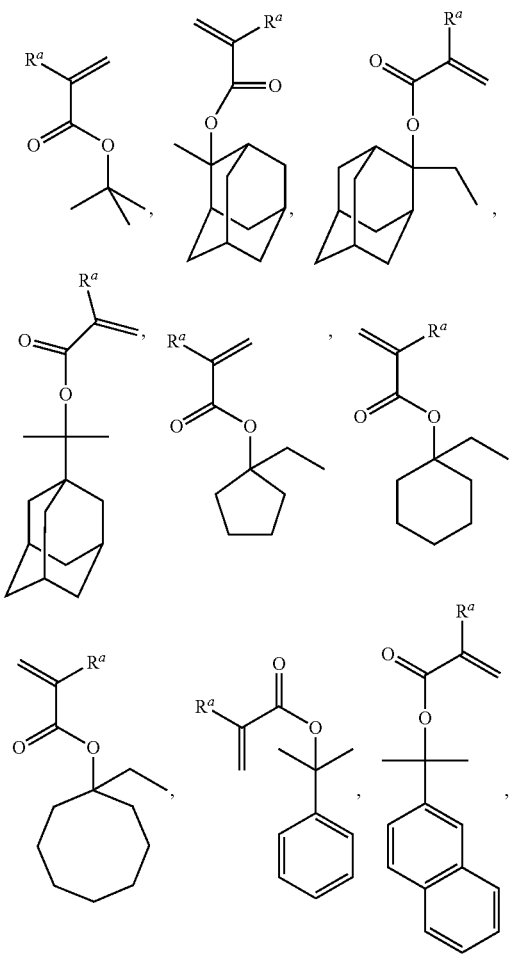

or a combination comprising at least one of the foregoing, wherein $R^a$ is H, F, —CN, $C_{1-6}$ alkyl, or $C_{1-6}$ fluoroalkyl.

Suitable lactone monomers may be of the following formula (IX):

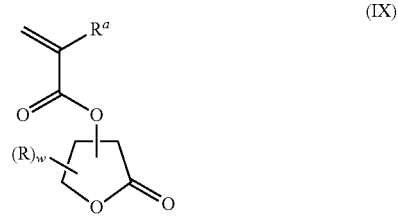

(IX)

wherein $R^a$ is H, F, —CN, $C_{1-6}$ alkyl, or $C_{1-6}$ fluoroalkyl, R is a $C_{1-10}$ alkyl, cycloalkyl, or heterocycloalkyl, and w is an integer of 0 to 5. In formula (IX), R is attached directly to the lactone ring or commonly attached to the lactone ring and/or one or more R groups, and the ester moiety is attached to the lactone ring directly, or indirectly through R.

Exemplary lactone-containing monomers include:

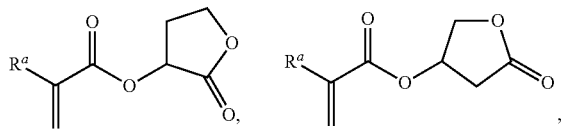

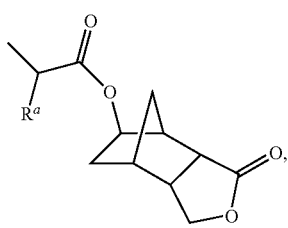

or a combination comprising at least one of the foregoing monomers, wherein $R^a$ is H, F, —CN, $C_{1-10}$ alkyl, or $C_{1-10}$ fluoroalkyl.

Suitable base-soluble monomers may be of the following formula (X):

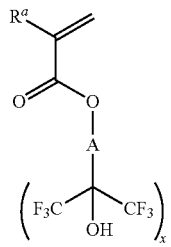

(X)

wherein each $R^a$ is independently H, F, —CN, $C_{1-10}$ alkyl, or $C_{1-10}$ fluoroalkyl, A is a hydroxyl-containing or non-hydroxyl containing, ester-containing or non ester-containing, fluorinated or non-fluorinated $C_{1-20}$ alkylene, $C_{3-20}$ cycloalkylene, $C_{6-20}$ arylene, or $C_{7-20}$ aralkylene, and x is an integer of from 0 to 4, wherein when x is 0, A is a hydroxyl-containing $C_{6-20}$ arylene.

Exemplary base soluble monomers include those having the following structures:

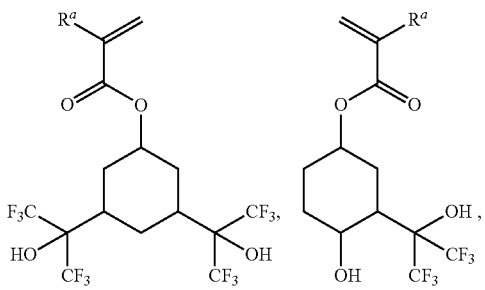

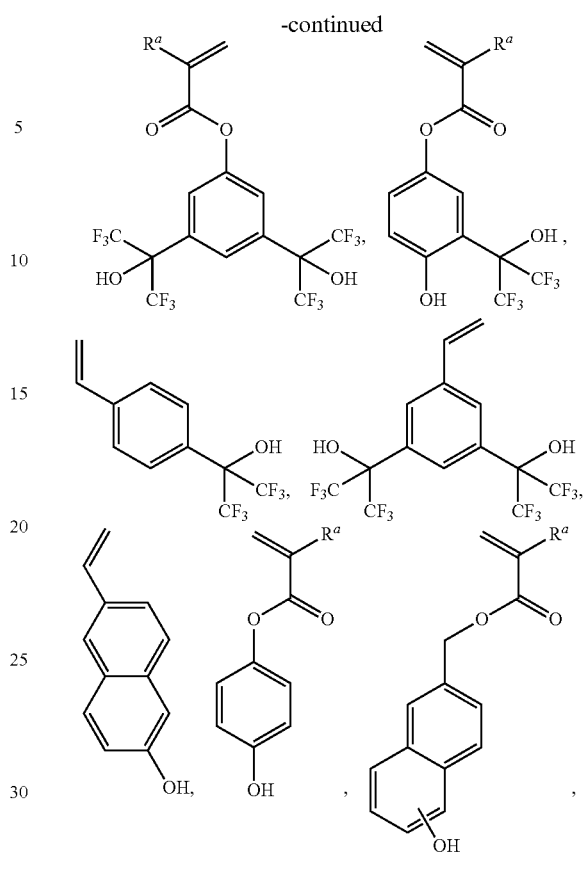

or a combination comprising at least one of the foregoing, wherein $R^a$ is H, F, —CN, $C_{1-6}$ alkyl, or $C_{1-6}$ fluoroalkyl.

Preferred acid generating monomers include those of the formulae (XI) or (XII):

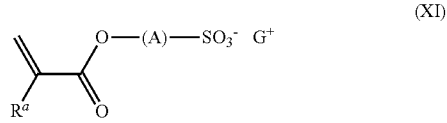

(XI)

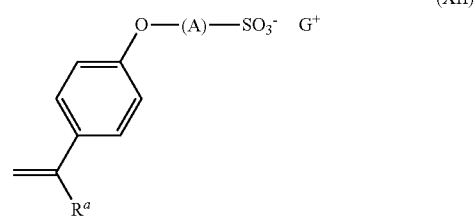

(XII)

wherein each $R^a$ is independently H, F, —CN, $C_{1-6}$ alkyl, or $C_{1-6}$ fluoroalkyl, A is a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group, and $G^+$ is a sulfonium or iodonium cation.

Preferably, in formulas (XI) and (XII), A is a —[(C$(R^1)_2)_xC(=O)O]_b$—C$((R^2)_2)_y(CF_2)_z$— group, or an o-, m- or p-substituted —$C_6F_4$— group, where each $R^1$ and $R^2$ are each independently H, F, —CN, $C_{1-6}$ fluoroalkyl, or $C_{1-6}$ alkyl, b is 0 or 1, x is an integer of 1 to 10, y and z are independently integers of from 0 to 10, and the sum of y+z is at least 1.

Exemplary preferred acid generating monomers include:

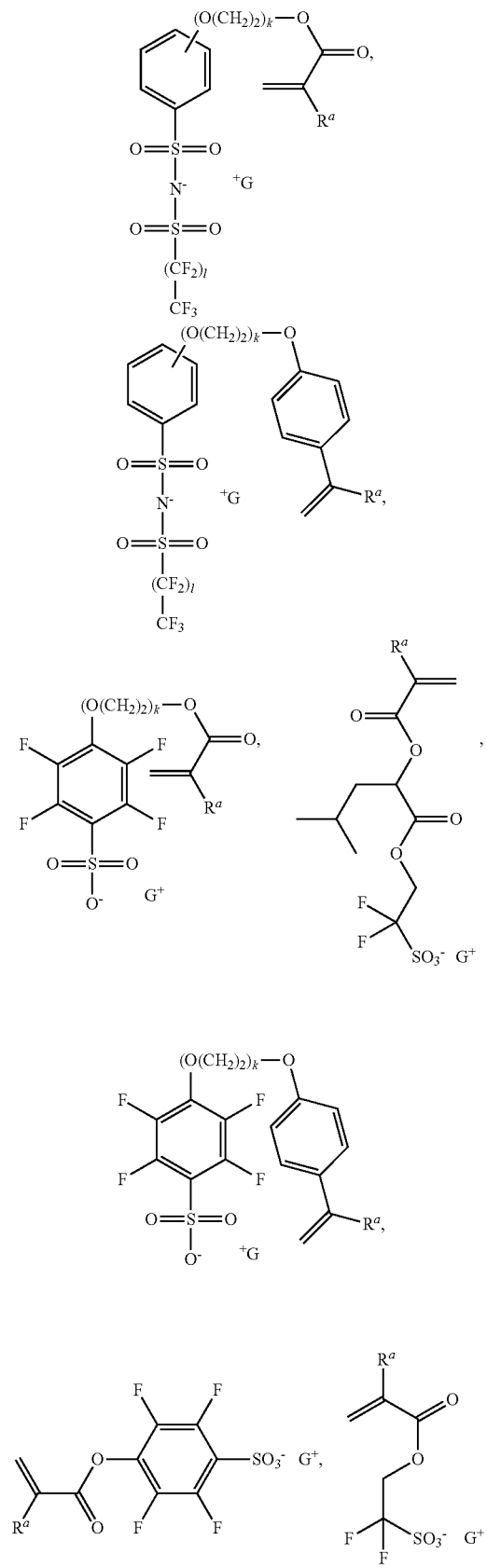

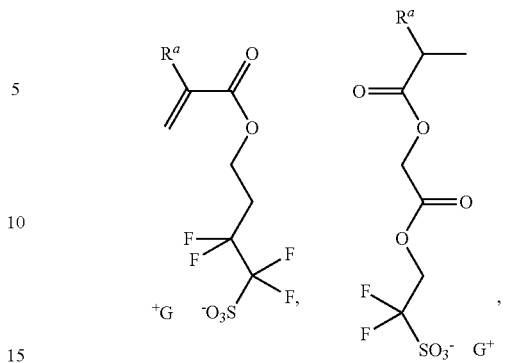

or a combination comprising at least one of the foregoing, where each $R^a$ is independently H, F, —CN, $C_{1-6}$ alkyl, or $C_{1-6}$ fluoroalkyl, k is suitably an integer of from 0 to 5; and $G^+$ is a sulfonium or iodonium cation. $G^+$ as referred to herein throughout the various formulae may be an acid generator as disclosed herein and comprise an oxo-dioxolane moiety and/or an oxo-dioxane moiety.

Preferred acid-generating monomers may include sulfonium or iodonium cation. Preferably, in formula (IV), $G^+$ is of the formula (XIII):

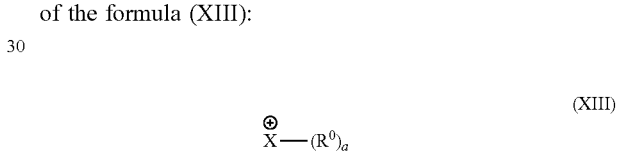

(XIII)

wherein X is S or I, each $R^0$ is halogenated or non-halogenated and is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, wherein when X is S, one of the $R^0$ groups is optionally attached to one adjacent $R^0$ group by a single bond, and a is 2 or 3, wherein when X is I, a is 2, or when X is S, a is 3.

Exemplary acid generating monomers include those having the formulas:

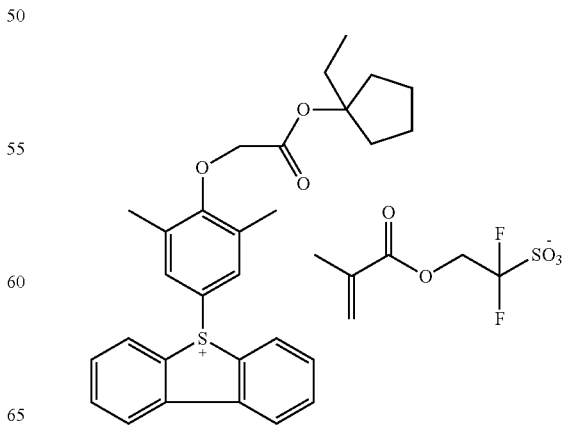

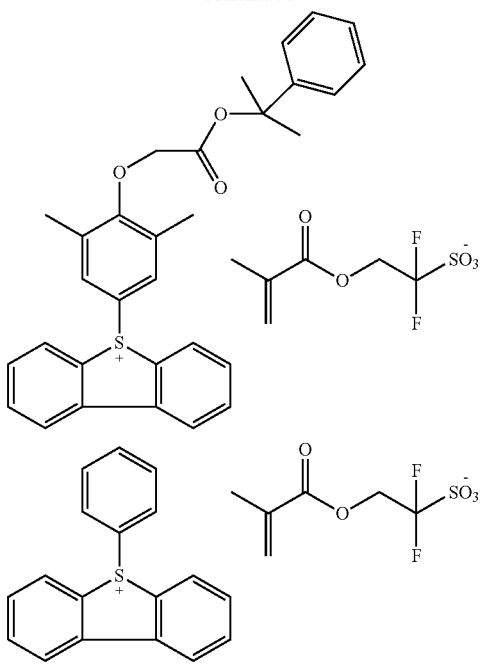
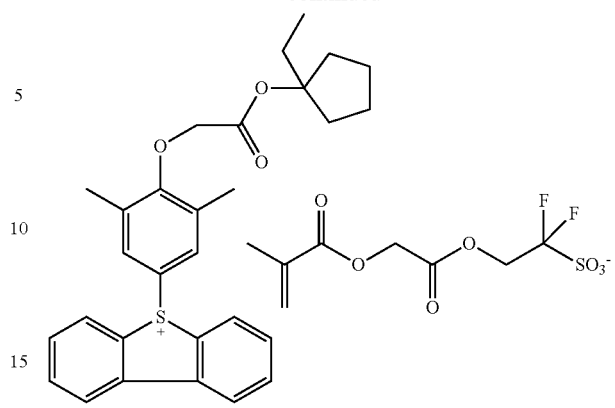
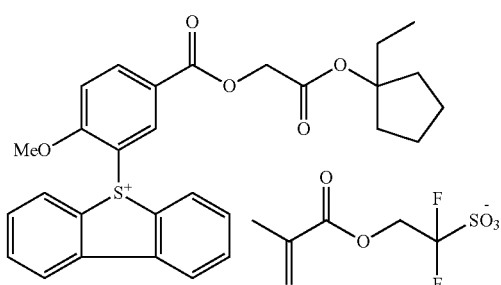
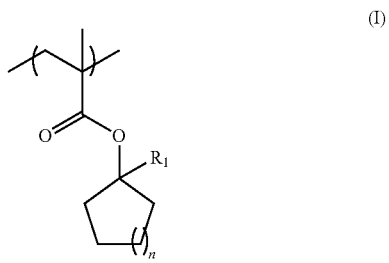
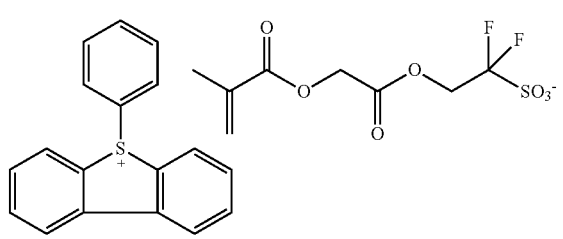
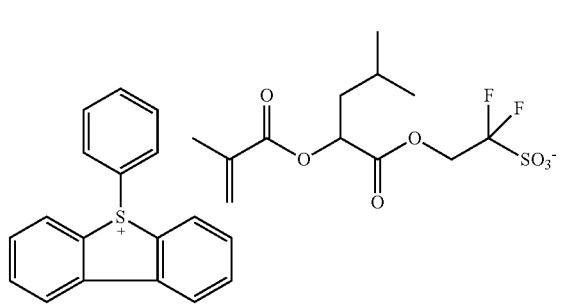

Specifically suitable polymers that have acid-labile deblocking groups for use in a positive-acting chemically-amplified photoresist of the invention have been disclosed in European Patent Application 0829766A2 (polymers with acetal and ketal polymers) and European Patent Application EP0783136A2 (terpolymers and other copolymers including units of 1) styrene; 2) hydroxystyrene; and 3) acid labile groups, particularly alkyl acrylate acid labile groups.

Additional preferred resins for use in photoresists to be imaged at sub-200 nm, such as at 193 nm, comprises units of the following general formulae (I), (II) and (III):

Preferred resins for use in photoresists to be imaged at sub-200 nm, such as at 193 nm, comprises units of the following general formulae (I), (II) and (III):

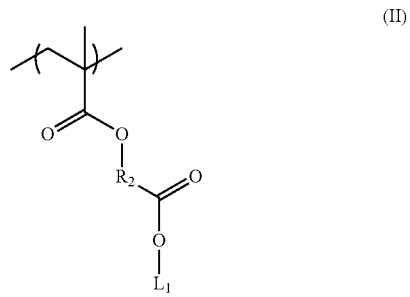

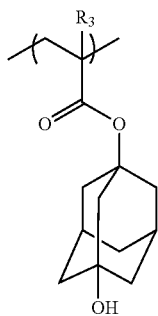

(III)

wherein: $R_1$ is a $(C_1-C_3)$alkyl group; $R_2$ is a $(C_1-C_3)$alkylene group; $L_1$ is a lactone group; and n is 1 or 2.

Polymers for use in photoresists of the invention may suitably vary widely in molecular weight and polydisperity. Suitable polymers include those that have an $M_w$ of from about 1,000 to about 50,000, more typically about 2,000 to about 30,000 with a molecular weight distribution of about 3 or less, more typically a molecular weight distribution of about 2 or less.

Preferred negative-acting compositions of the invention comprise a mixture of materials that will cure, crosslink or harden upon exposure to acid, and two or more acid generators as disclosed herein. Preferred negative acting compositions comprise a polymer binder such as a phenolic or non-aromatic polymer, a crosslinker component and a photoactive component of the invention. Such compositions and the use thereof have been disclosed in European Patent Applications 0164248 and U.S. Pat. No. 5,128,232 to Thackeray et al. Preferred phenolic polymers for use as the polymer binder component include novolaks and poly(vinylphenol)s such as those discussed above. Preferred crosslinkers include amine-based materials, including melamine, glycolurils, benzoguanamine-based materials and urea-based materials. Melamine-formaldehyde polymers are often particularly suitable. Such crosslinkers are commercially available, e.g. the melamine polymers, glycoluril polymers, urea-based polymer and benzoguanamine polymers, such as those sold by Cytec under tradenames Cymel 301, 303, 1170, 1171, 1172, 1123 and 1125 and Beetle 60, 65 and 80.

Particularly preferred photoresists of the invention may be used in immersion lithography applications. See, for example, U.S. Pat. No. 7,968,268 to Rohm and Haas Electronic Materials for a discussion of preferred immersion lithography photoresists and methods. Preferred photoresists for use in immersion application may comprise a resin (which may be fluorinated and/or have acid-labile groups) that is separate (not covalently linked) and distinct from a primary resin that has photoacid-labile groups. Thus, the present invention includes in preferred aspects photoresists that comprise: 1) a first resin with acid-labile groups; 2) one or more acid generator compounds; 3) a second resin that is separate and distinct from the first resin, the second resin may be fluorinated and/or have acid-labile groups; and 4) one or more carbamate compounds as disclosed herein.

Photoresists of the invention also may comprise a single acid generator or a mixture of distinct acid generators, typically a mixture of 2 or 3 different acid generators, more typically a mixture that consists of a total of 2 distinct acid generators. The photoresist composition comprises a acid generator employed in an amount sufficient to generate a latent image in a coating layer of the composition upon exposure to activating radiation. For example, the acid generator will suitably be present in an amount of from 1 to 20 wt % based on total solids of the photoresist composition. Typically, lesser amounts of the acid generator be suitable for chemically amplified resists as compared with non-chemically amplified materials.

Suitable acid generators are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl-p-toluenesulfonate, 2,6-dinitrobenzyl-p-toluenesulfonate, and 2,4-dinitrobenzyl-p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenesulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine.

As referred to herein, acid generators can produce an acid when exposed to activating radiation, such as EUV radiation, e-beam radiation, 193 nm wavelength radiation or other radiation sources. Acid generator compounds as referred to herein also may be referred to as photoacid generator compounds.

Photoresists of the invention suitably may comprise one or more carbamate compounds as disclosed herein in a wide amount range, such as from 0.005 to 15 wt %, based on the weight of the acid generator, preferably from 0.01 to 15 wt %, and even more preferably from 0.01 to 10 wt %. The added carbamate component is suitably used in amounts of 0.01, 0.05, 0.1, 0.02, 0.3, 0.4, 0.5 or 1 to 10 or 15 wt % relative to the acid generator, and more typically amounts of 0.01, 0.05, 0.1, 0.02, 0.3, 0.4, 0.5 or 1 to 5, 6, 7, 8, 9 or 10 weight percent.

Photoresists of the invention also may contain other materials. For example, other optional additives include actinic and contrast dyes, anti-striation agents, plasticizers, speed enhancers and sensitizers. Such optional additives typically will be present in minor concentration in a photoresist composition.

Alternatively, or in addition, other additives may include quenchers that are non-photo-destroyable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as tripropylamine, dodecylamine, tris(2-hydroxypropyl)amine, oltetrakis (2-hydroxypropyl)ethylenediamine; aryl amines such as diphenylamine, triphenylamine, aminophenol, and 2-(4-aminophenyl)-2-(4-hydroxyphenyl)propane, Troger's base, a hindered amine such as diazabicycloundecene (DBU) or diazabicyclononene (DBN), or ionic quenchers including quaternary alkyl ammonium salts such as tetrabutylammonium hydroxide (TBAH) or tetrabutylammonium lactate.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist further includes a solvent generally suitable for dissolving, dispensing, and coating the components used in a photoresists. Exemplary solvents include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Such photoresists may include the polymer in an amount of 50 to 99 wt %, specifically 55 to 95 wt %, more specifically 60 to 90 wt %, and still more specifically 65 to 90 based on the total weight of solids. The photo-destroyable base may be present in the photoresist in an amount of 0.01 to 5 wt %, specifically 0.1 to 4 wt %, and still more specifically 0.2 to 3 wt %, based on the total weight of solids. A surfactant may be included in an amount of 0.01 to 5 wt %, specifically 0.1 to 4 wt %, and still more specifically 0.2 to 3 wt %, based on the total weight of solids. A quencher may be included in relatively small amounts of for example, from 0.03 to 5 wt % based on the total weight of solids. Other additives may be included in amounts of less than or equal to 50 wt %, specifically less than or equal to 35%, or more specifically less than or equal to 25%, based on the total weight of solids. The total solids content for the photoresist composition may be 0.5 to 50 wt %, specifically 1 to 45 wt %, more specifically 2 to 40 wt %, and still more specifically 5 to 30 wt %, based on the total weight of solids and solvent. The acid generators should be present in an amount sufficient to enable generation of a latent image in a coating layer of the resist. More specifically, the two or more acid generators will suitably be present in an amount of from about 1 to 50 weight percent of total solids of a resist. It will be understood that the solids includes polymer, quencher, surfactant, and any optional additives, exclusive of solvent.

A coated substrate may be formed from the photoresist containing acid generators which should be present in an amount sufficient to enable generation of a latent image in a coating layer of the resist and acid generators. Such a coated substrate includes: (a) a substrate having one or more layers to be patterned on a surface thereof; and (b) a layer of the photoresist composition including the acid generator over the one or more layers to be patterned. For EUV or e-beam imaging, photoresists may suitably have relatively higher content of acid generator compounds, e.g. where the one or more acid generators comprise 5 to 10 to about 65 weight percent of total solids of the resist. Typically, lesser amounts of the photoactive component will be suitable for chemically amplified resists.

The photoresists of the invention are generally prepared following known procedures with the exception that one or more acid generator compounds of the invention are substituted for prior photoactive compounds used in the formulation of such photoresists. The photoresists of the invention can be used in accordance with known procedures.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 20 cm, 30 cm, or larger in diameter, or other dimensions useful for wafer fabrication production.

Further, a method of forming an electronic device includes (a) applying a layer of a photoresist composition including on a surface of the substrate; (b) patternwise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 1,000 to 2,500 rpm. The coated wafer is spun to remove solvent, and baked on a hot plate to remove residual solvent and free volume from the film to make it uniformly dense.

Patternwise exposure is then carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet (EUV) or e-beam radiation. It will be appreciated that exposure using the activating radiation decomposes the acid generator in the exposed areas and generates acid and decomposition by-products, and that the acid then effects a chemical change in the polymer (deblocking the acid sensitive group to generate a base-soluble group, or alternatively, catalyzing a cross-linking reaction in the exposed areas). The resolution of such exposure tools may be less than 30 nm.

Developing the exposed photoresist layer is then accomplished by treating the exposed layer to a suitable developer capable of selectively removing the exposed portions of the film (where the photoresist is positive tone) or removing the unexposed portions of the film (where the photoresist is crosslinkable in the exposed regions, i.e., negative tone). Preferably, the photoresist is positive tone based on a polymer having acid sensitive (deprotectable) groups, and the developer is preferably a metal-ion free tetraalkylammonium hydroxide solution, such as, for example, aqueous 0.26 N tetramethylammonium hydroxide. A pattern forms by developing.

Additionally, for positive resists, unexposed regions can be selectively removed by treatment with a suitable nonpolar solvent for negative tone development. See U.S. 2011/0294069 for suitable procedures for negative tone development of positive photoresists. Typical nonpolar solvents for negative tone development are organic developers, such as a solvent chosen from ketones, esters, hydrocarbons, and mixtures thereof, e.g. acetone, 2-hexanone, methyl acetate, butyl acetate, and tetrahydrofuran.

The photoresist may, when used in one or more such a pattern-forming processes, be used to fabricate electronic and optoelectronic devices such as memory devices, processor chips (CPU's), graphics chips, and other such devices.

Example 1: Synthesis of 1,2-di-tert-butyl pyrrolidine-1,2-dicarboxylate

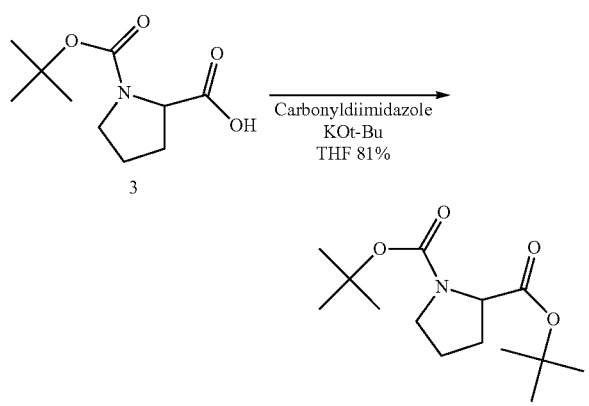

To 30.00 g (139 mmol) 1-(tert-butoxycarbonyl)pyrrolidine-2-carboxylic acid in 140 mL THF was added at ambient temperature under nitrogen carbonyldiimidazole (23.67 g, 1.05 eq.) and the reaction stirred until gas evolution ceased. The reaction was heated at 65° C. for 2 h., cooled to ambient temperature, and added slowly into a −78° C. 1 M solution of potassium tert-butoxide in THF. The reaction was allowed to warm slowly to ambient temperature overnight, then poured into 500 mL water, acidified to pH 8 with 1N HCl, saturated with NaCl, and extracted into 1 L iPrOAc. The organic phase was separated, washed with 1.4 L 0.1N ammonium chloride, 500 mL water, and 250 mL NaHCO$_3$ $_{(sat\ aq.)}$, and dried on Na$_2$SO$_4$. The solvent was removed in-vacuo to give 30.44 g (81%) of the desired product as an amber oil.

Example 2: Synthesis of 1-tert-butyl 2-(1-ethylcyclopentyl) pyrrolidine-1,2-dicarboxylate

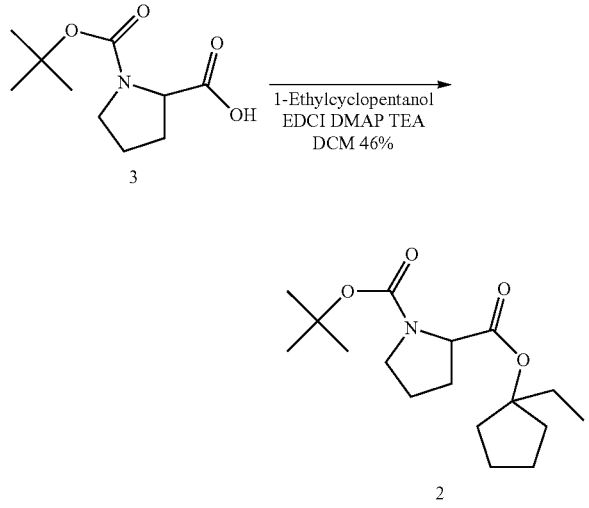 [SMILES: CC(C)(C)OC(=O)N1CCCC1C(=O)O ; CCC1(OC(=O)C2CCCN2C(=O)OC(C)(C)C)CCCC1]

To 30.00 g (139 mmol) 1-(tert-butoxycarbonyl)pyrrolidine-2-carboxylic acid in 50 mL DCM added 21.3 mL (1.1 eq.) TEA, then EDCI (29.33 g, 1.1 eq), DMAP (18.69 g, 1.1 eq) and 140 mL 1-ethylcyclopentanol. The reaction was stirred 16 h at ambient temperature under nitrogen, solvent removed under high vacuum at 80° C., and the residue dissolved in 2 L iPrOAc. The organic phase was washed three times with 2 L 0.1 N HCl and 500 mL NaHCO$_{3(sat\ aq.)}$, dried on Na$_2$SO$_4$, and the solvent removed in-vacuo. The residue was dissolved in 100 mL DCM and filtered through a dry plug of 170 g silica. The silica was eluted with 500 mL DCM and the solvent removed in-vacuo to give 20.00 g (46%) as a clear oil.

Example 3: Photoresist Preparation and Lithographic Processing

Four photoresists were formulated using the components shown below in Table 1 as weight percent based on 100% solids content, with the balance of the solids being the polymer.

TABLE 1

| Example | Polymer | Acid Generator (AG) | Base | SLA | PGMEA (w/w of solvent) | HBM (w/w of solvent) | % solids |
|---|---|---|---|---|---|---|---|
| Comp. Ex. 1 | Polymer 1 (100) | AG1 (10%) | Base 1 (1%) | PF656 (0.1%) | 50 | 50 | 4 |
| Comp. Ex. 2 | Polymer 1 (100) | AG1 (10%) | Base 2 (1%) | PF656 (0.1%) | 50 | 50 | 4 |
| Ex. 1 | Polymer 1 (100) | AG1 (10%) | Base 3 (1.35%) | PF656 (0.1%) | 50 | 50 | 4 |
| Ex. 2 | Polymer 1 (100) | AG1 (10%) | Base 4 (1.55%) | PF656 (0.1%) | 50 | 50 | 4 |

Polymer 1: IAM/ECPMA/ODOTMA/a/HAMA (20/20/30/20/10) and has Mw of 8000.

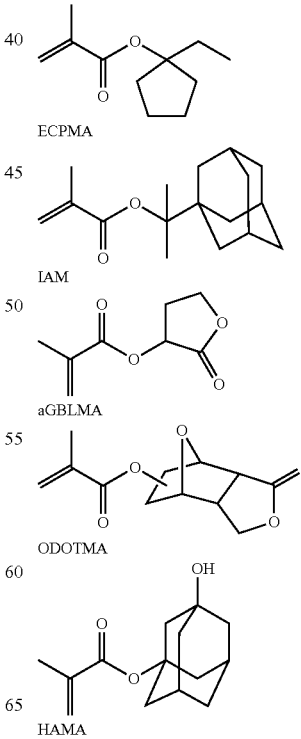

TABLE 1-continued

| Example | Polymer | Acid Generator (AG) | Base | SLA | PGMEA (w/w of solvent) | HBM (w/w of solvent) | % solids |
|---|---|---|---|---|---|---|---|

AG 1: triphenylsulfonium 1'-adamantanemethoxycarbonyl-2,2-difluoromethanesulfonate Base 1: N-t-butyloxycarbonyl-4-hydroxypiperidine Base 2: N-t-butyloxycarbonyl-trishydroxymethylmethylamine Base 3: 1,2-Pyrrolidinedicarboxylic acid, 1,2-bis(1,1-dimethylethyl) ester Base 4: 1,2-Pyrrolidinedicarboxylic acid, 1-(1,1-dimethylethyl) 2-(1'-ethylcyclopentyl) ester Surface Leveling Agent (SLA): Fluorinated (PF 656)

The formulated photoresists were spin coated using TEL ACT-8 (Tokyo Electron) coating track onto a 200 mm silicon wafer having as bottom antireflective coating (BARC) (AR™77, Dow Electronic Materials), and soft baked at 110° C. for 60 seconds, to form a resist film of about 100 nm in thickness. The photoresist layer was exposed using an ASML/1100, 0.75 NA stepper operating at 193 nm through a photomask with PSM feature size of 90 nm 1:1 Line/Space pattern, under Annular illumination with outer/inner sigma of 0.89/0.64 with focus offset/step 0.10/0.05. The exposed wafers were post-exposed baked (PEB) at 100° C. for 60 seconds. The coated wafers were next treated with a metal ion free base developer (0.26N aqueous tetramethylammonium hydroxide solution) to develop the photoresist layer. Line Width Roughness (LWR) was determined by processing the image captured by top-down scanning electron microscopy (SEM) using a Hitachi 9380 CD-SEM, operating at an accelerating voltage of 800 volts (V), probe current of 8.0 picoamperes (pA), using 200 Kx magnification. LWR was measured over a 2 µm line length in steps of 40 nm, and reported as the average for the measured region. Results are shown in the following Table 2.

TABLE 2

| Photoresist | Eo | EL % | LWR |
|---|---|---|---|
| Comp. Ex. 1 | 10 | Bad | Bad |
| Comp. Ex. 2 | 9.6 | Bad | Bad |
| Ex. 1 | 9.6 | Good | Good |
| Ex. 2 | 9.6 | Good | Good |

In Table 2, Eo (Energy to clear is the exposure dose in mJ/cm2 of 193 wavelength radiation required to remove bulk film.

In Table 2, LWR (Line width Roughness) is defined as the length width over a range of spatial frequencies. The lower the LWR value, the smoother the line.

EL % is determined by measuring the ratio of exposure dose range within ±10% of CD over exposure dose.

What is claimed is:

1. A photoresist composition comprising:
   (a) a resin;
   (b) an acid generator; and
   (c) a non-polymeric carbamate compound that comprises i) a carbamate group and ii) an ester group,
   wherein the carbamate compound corresponds to a structure of the following Formula I:

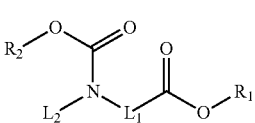

wherein:
   R1 and R2 are each the same or different non-hydrogen substituent;
   L1 is a linker group that comprises at least one carbon atom;
   L2 is a non-hydrogen substituent;
and wherein:
   L2 and R2 may be optionally taken together to form a ring structure;
   L1 and L2 may be optionally taken together to form a ring structure;
   R1 and L1 or R1 and L2 may be optionally taken together to form a ring structure; and
   both of R1 and R2 comprises an acid-labile moiety.

2. The photoresist composition of claim 1 wherein at least one of R1 and R2 comprises a tertiary alkyl group, and/or at least one of R1 and R2 comprises an acetal or ketal group.

3. The photoresist composition of claim 1 wherein L2 and R2 are taken together to form a ring structure; L1 and L2 are taken together to form a ring structure; or R1 and L1 or R1 and L2 are taken together to form a ring structure.

4. The photoresist composition of claim 1 wherein the photoresist comprises one or more of the following:

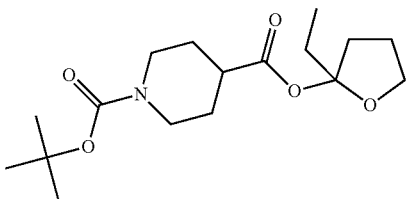 [SMILES: CCC1(OC(=O)C2CCN(C(=O)OC(C)(C)C)CC2)CCCO1]

US 10,539,870 B2
29
-continued
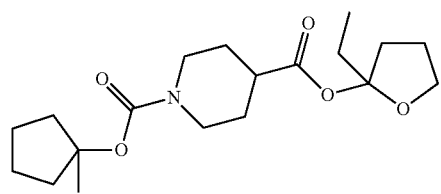
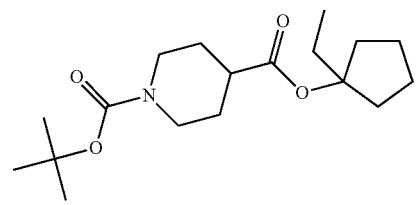
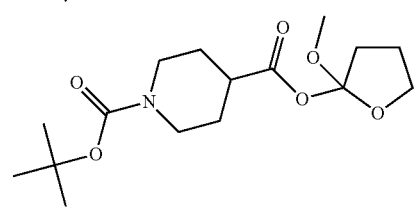
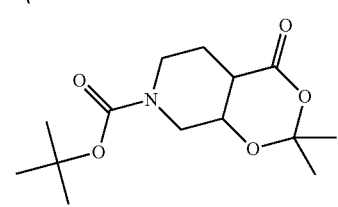
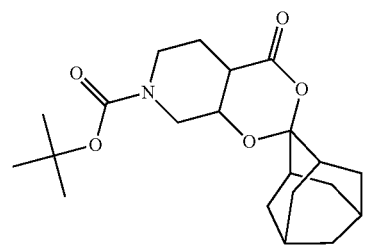
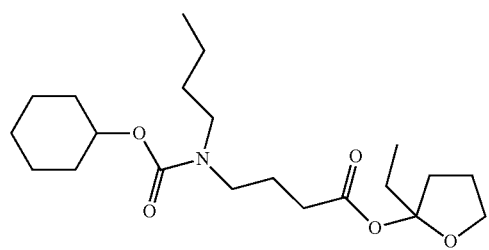
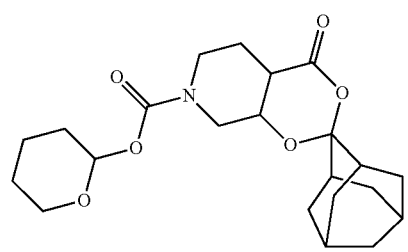
30
-continued
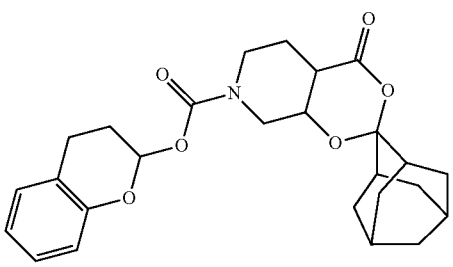
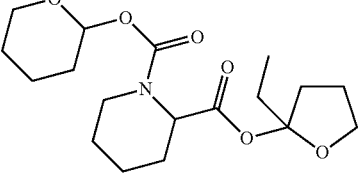
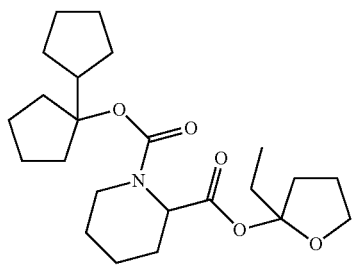
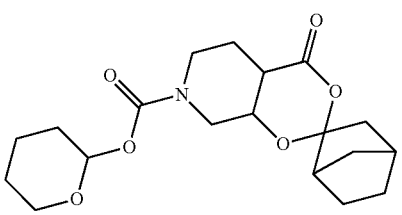 [SMILES: O=C1OC2(CC3CCC2C3)OC2CN(C(=O)OC3CCCCO3)CCC12]
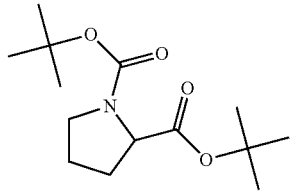
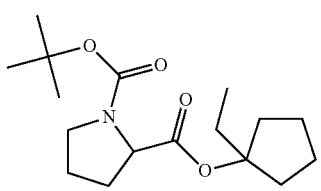

31
-continued

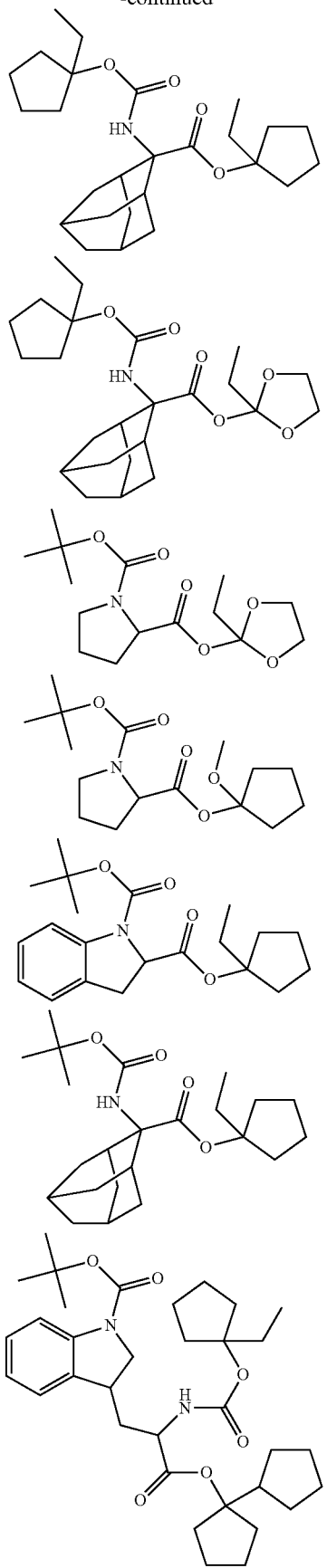

32
-continued

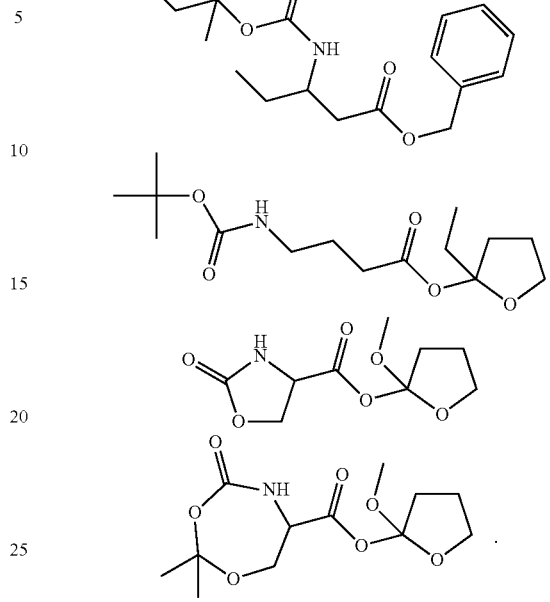

5. The photoresist composition of claim 1 wherein the carbamate compound comprises both 1) a carbamate group that comprises an acid-labile moiety and 2) an ester group that comprises an acid-labile moiety.

6. The photoresist composition of claim 1 wherein the carbamate compound corresponds to a structure of the following Formula IA:

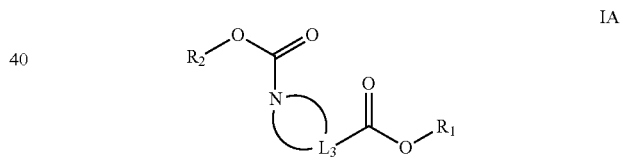

IA wherein in Formula IA, R1 and R2 are each the same or different non-hydrogen substituent;
the depicted two semi-circular lines between N and L3 together represent an optionally substituted single-ring or multiple-ring structure having 5 to 20 atoms with N and one or more atoms of L3 being ring members; and L3 contains 1 to 16 carbon or hetero atoms.

7. The photoresist composition of claim 6 wherein L3 contains only carbon atoms.

8. The photoresist composition of claim 1 wherein L2 and R2 are taken together to form a ring structure.

9. The photoresist composition of claim 1 wherein L1 and L2 are taken together to form a ring structure.

10. The photoresist composition of claim 1 wherein R1 is part of an ester acid-labile group with the OC(=O)— moiety of Formula I.

11. The photoresist composition of claim 1 wherein L2 an R2 are taken together to form a ring structure; L1 and L2 are taken together to form a ring structure; or R1 and L1 or R1 and L2 are taken together to form a ring structure.

12. A method for forming a photoresist relief image comprising:

(a) applying a coating layer of a photoresist composition of claim 1 on a substrate;

(b) exposing the photoresist coating layer to patterned activating radiation and developing the exposed photoresist layer to provide a relief image.

13. The method of claim 12 wherein the activating radiation is EUV or electron-beam radiation.

14. A photoresist composition comprising:

(a) a resin;

(b) an acid generator; and (c) a carbamate compound that comprises a structure of the following Formulae IB or IC:

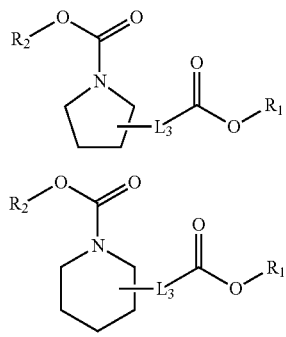

wherein in each of Formulae IB and IC, R1 and R2 are each the same or different non-hydrogen substituent; and L3 contains 1 to 16 carbon or hetero atoms.

15. The photoresist composition of claim 14 wherein L3 contains only carbon atoms.

16. The photoresist composition of claim 15 wherein the carbamate compound corresponds to a structure of Formula IB.

17. The photoresist composition of claim 15 wherein the carbamate compound corresponds to a structure of Formula IC.

18. The photoresist composition of claim 14 wherein the carbamate compound corresponds to a structure of Formula IB.

19. The photoresist composition of claim 14 wherein the carbamate compound corresponds to a structure of Formula IC.

20. A method for forming a photoresist relief image comprising:

(a) applying a coating layer of a photoresist composition of claim 4 on a substrate;

(b) exposing the photoresist coating layer to patterned activating radiation and developing the exposed photoresist layer to provide a relief image.

21. A photoresist composition comprising:

(a) a resin;

(b) an acid generator; and (c) a non-polymeric carbamate compound that comprises i) a carbamate group and ii) an ester group, wherein the carbamate compound corresponds to a structure of the following Formula I:

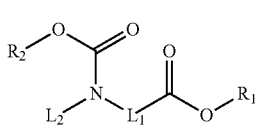

wherein:
R1 and R2 are each the same or different non-hydrogen substituent;
L1 is a linker group that comprises at least one carbon atom;
L2 is a non-hydrogen substituent;
and wherein at least one of R1 and R2 comprises an acid-labile moiety, and at least one of R1 and R2 comprises an acetal or ketal group.

22. The photoresist composition of claim 21 wherein both of R1 and R2 comprise an acid-labile moiety.

23. The photoresist composition of claim 21 wherein at least one of R1 and R2 comprises a tertiary alkyl group.

24. A photoresist composition comprising:

(a) a resin;

(b) an acid generator; and (c) a non-polymeric carbamate compound that comprises i) a carbamate group and ii) an ester group;

wherein the carbamate compound corresponds to a structure of the following Formula I:

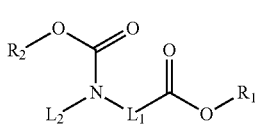

wherein:
R1 and R2 are each the same or different non-hydrogen substituent;
L1 is a linker group that comprises at least one carbon atom;
L2 is a non-hydrogen substituent;
and wherein:
L2 and R2 are taken together to form a ring structure;
L1 and L2 may be optionally taken together to form a ring structure;
R1 and L1 or R1 and L2 may be optionally taken together to form a ring structure; and
at least one of R1 and R2 comprises an acid-labile moiety.

* * * * *